United States Patent [19]
Billings et al.

[11] 3,931,344
[45] Jan. 6, 1976

[54] BROMOFLUOROCYCLOPROPANES

[75] Inventors: Charles Alden Billings, Concord; Gerald Joseph O'Neill, Arlington; Charles William Simons, Bedford; Robert S. Holdsworth, Arlington, all of Mass.

[73] Assignee: W. R. Grace & Co., Cambridge, Mass.

[22] Filed: Dec. 26, 1974

[21] Appl. No.: 536,573

Related U.S. Application Data

[63] Continuation-in-part of Ser. No. 499,761, Aug. 22, 1974.

[52] U.S. Cl. ............................. 260/648 F; 424/352
[51] Int. Cl.² ......................................... C07C 23/04
[58] Field of Search ................................. 260/648 F

[56] References Cited
UNITED STATES PATENTS
3,865,950   2/1975   O'Neill et al. ................... 260/648 F

OTHER PUBLICATIONS

Seyferth et al., Chem. Abstracts 78, 159781n, (1973).

Chem. Abstracts, Vol. 78, Chemical Substance Index, 1368 CS Rt. Hand Column (1973).

Primary Examiner—D. Horwitz
Attorney, Agent, or Firm—Armand McMillan; C. E. Parker

[57] ABSTRACT

The following newly synthesized bromofluoromethylcyclopropanes have been found to possess utility as general inhalation anesthetics: 1-bromo-1,2-difluoro-2-methylcyclopropane and 1-bromo-1-fluoro-2-methylcyclopropane.

1 Claim, No Drawings

BROMOFLUOROCYCLOPROPANES

RELATED APPLICATION

This application is a continuation-in-part of application Ser. No. 499,761 filed on Aug. 22, 1974.

THE PRIOR ART

Although a certain number of halogenated hydrocarbon compounds, including some bromocyclopropanes and methylcyclopropanes, have joined the ranks of useful anesthetics in the recent past, little has been added to the understanding of the mode of action of chemicals in this physiological role, so that the relationships of the structural differences between fairly similar compounds with either their deleterious, inert or therapeutic properties remain substantially unidentified. At this stage in the art, therefore, the discovery of additional substances possessing a desirable combination of physical, chemical and physiological properties for anesthetic purposes still lies beyond the scope of routine expertise.

SUMMARY OF THE INVENTION

It has now been discovered that two newly synthesized bromofluoromethylcyclopropanes possess high potency as general anesthetics when administered in inhalation-anesthetic-susceptible organisms. They are: 1-bromo-1,2-difluoro-2-methylcyclopropane and 1-bromo-1-fluoro-2-methylcyclopropane.

DETAILED DESCRIPTION

The compounds which constitute the basis of this invention may be prepared by any of several methods depending on the availability of starting materials and on the yield considered acceptable under the circumstances. These methods ultimately involve a catalyzed cyclization reaction between a suitable halocarbene (:CZY) and an appropriate olefinic compound:

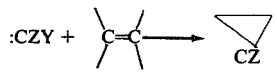

The halocarbene can be generated by the decomposition of the appropriate phenyl (trihalomethyl) mercury compound, according to the method of D. Seyferth et al. [J. Am. Chem. Soc. 87, 4259–70 (1965)]. However, the actual method employed in the present instance, as described in the following examples, is an adaptation of a known procedure for the general synthesis of gem-dihalocyclopropanes [Synthesis 2, 112 (1973)].

The methylbromocyclopropanes of the invention were prepared by the cyclization of the carbene :CFBr with an appropriate olefin. The carbene was prepared in concentrated sodium hydroxide solution from dibromofluoromethane with the assistance of an ionic salt such as triethylbenzlammonium bromide. The reactions involved are:

$R_4N^+X^- + OH^- \rightarrow R_4N^+O^-H + X^-$  (1)
$CHFBr_2 + R_4N^+O^-H \rightleftharpoons CF^-Br_2R_4N^+ + H_2O$  (2)
$CFBr_2R_4N^+ \rightarrow :CFBr + R_4N^+Br^-$  (3)

The quaternary ammonium hydroxide formed (1), being insoluble in the reaction mixture, migrates to the boundary between the aqueous and the organic phases where it reacts with the trihalomethane to yield the quaternary ammonium derivative of the trihalomethyl anion (2). After diffusion into the organic phase, the derivative is transformed (3) into the carbene :CFBr and the catalyst halide. The carbene then reacts with the olefin to yield a cyclopropane. The olefins used and the products obtained are listed in Table I.

EXAMPLE 1

1-Bromo-1,2-difluoro-2-methylcyclopropane can be prepared as follows: 50% aqueous sodium hydroxide, 125 ml, is placed in a 300 ml stainless steel autoclave with triethylbenzylammonium bromide, 1.0 g, dibromofluoromethane, 0.60 mole, and 2-fluoropropene, 0.70 mole. The contents of the autoclave are stirred at ambient temperature until all the halogenated methane has been consumed, in this case a period of about 24 hours. The reaction mixture is then vacuum distilled to collect the organic phase and the distillate is further refined by redistillation after separation of entrained water. Clear colorless liquid 1-bromo-1,2-difluoro-2-methylcyclopropane is obtained, as identified by specific gravity and boiling point (Table 2), in a yield of 35%, based on the methane.

EXAMPLE 2

1-Bromo-1-fluoro-2-methylcyclopropane can be prepared in the manner of Example 1, except that propylene is used instead of its 2-fluoro analog. A yield of 29% was obtained, based on the methane.

The olefinic starting material and the product obtained in this and the other example are listed in the following table.

TABLE 1
PREPARATION OF METHYLBROMOFLUOROCYCLOPROPANES

| Ex. | Olefin | Product | | | |
|---|---|---|---|---|---|
| | | Yield* | Mol. Wt. | Spec. Gravity | Boiling Point |
| 1 | 2-Fluoropropene | 1-Br-1,2-diF-2-methylcyclopropane | | | |
| | | 34% | 171.00 | 1.568[20] | 90° |
| 2 | Propylene | 1-Br-1-F-2-methylcyclopropane | | | |
| | | 29% | 153.01 | 1.458[20] | 85° |

*These yields are calculated on dibromofluoromethane basis.

The cyclopropanes shown in Table 1 are clear liquids at room temperature. They can be stored in containers of the type commonly used for conventional anesthetics of comparable boiling point, e.g. halothane, and they can be administered by means of apparatus or machines designed to vaporize liquid anesthetics and mix them with air, oxygen or other gaseous combinations in proportions capable of supporting respiration.

EXAMPLES 3 and 4

The physiological effects of the cyclopropanes prepared in the preceding examples were demonstrated as follows, using a standard test for evaluation of inhalation anesthetics similar to that described in Robbins [J. Pharmacology and Experimental Therapeutics 86, 197 (1946)].

Mice were exposed to the anesthetic for a period of 10 minutes in a rotating drum. Observations were then made of the pinch reflex, the corneal reflex and the return of the righting reflex. At least four graded doses were employed to determine the minimum concentration required to anesthetize 50% of the mice used ($AC_{50}$) and the minimum concentration required to kill 50% of the mice ($LC_{50}$). The anesthetic index (AI) was then calculated from these minimum concentrations.

The results of these tests are summarized in the following table.

TABLE 2
ANESTHETIC PROPERTIES OF METHYLBROMOFLUOROCYCLOPROPANES

| Ex. | Cyclopropane | $AC_{50}$ (%) volume) | $LC_{50}$ | AI ($LC_{50}/AC_{50}$) |
| --- | --- | --- | --- | --- |
| 3 | 1-Br-1,2-diF-2-methyl | 0.5% | 5% | 10 |
| 4 | 1-Br-1-F-2-methyl | < 2% | >2 | 4–6%* |

*When two figures are given, the actual value lies between them.

As these results indicate, two new effective anesthetic agents have been contributed to the art. It is contemplated that they may be used in admixture with pharmaceutically acceptable diluents and stabilizers such as thymol, or in combination with one or more of the known inhalation anesthetics, e.g. nitrous oxide, ether, halothane, chloroform, methoxyflurane and the like. Other variations can be carried out in either preparation or the administration of the compounds to accomodate factors such as, for instance, economic considerations, level and duration of anesthesia desired and subject treated. Such variations fall within the scope of the present invention.

What we claim is:
1. 1-Bromo-1,2-difluoro-2-methylcyclopropane.

\* \* \* \* \*